United States Patent [19]

Krueger

[11] Patent Number: 4,818,227

[45] Date of Patent: Apr. 4, 1989

[54] SOUND PRODUCING INDICATORS USED IN COMBINATION WITH PNEUMATICALLY OPERATED MACHINES

[75] Inventor: Kenneth K. Krueger, Laguna Niguel, Calif.

[73] Assignee: Denar Corporation, Anaheim, Calif.

[21] Appl. No.: 147,242

[22] Filed: Jan. 21, 1988

[51] Int. Cl.⁴ ............................ A61C 1/00; A61C 3/00
[52] U.S. Cl. ....................................................... 433/27
[58] Field of Search .................... 433/27, 114; 408/16; 604/181

[56] References Cited

U.S. PATENT DOCUMENTS 4,559,577 12/1985 Shoji et al. ............................ 408/16
4,702,650 10/1987 Golwas et al. ........................ 408/16

*Primary Examiner*—Robert Peshock
*Attorney, Agent, or Firm*—Edward D. O'Brian

[57] ABSTRACT

A pneumatically operated machine such as a dental drill can be used with a pneumatically operated indicator capable of providing an audible signal such as a whistle or horn so provide an indication if the machine is stopped or is being operated in reverse. The indicator used is operated through the use of the pneumatic fluid normally used to operate the machine.

10 Claims, 1 Drawing Sheet

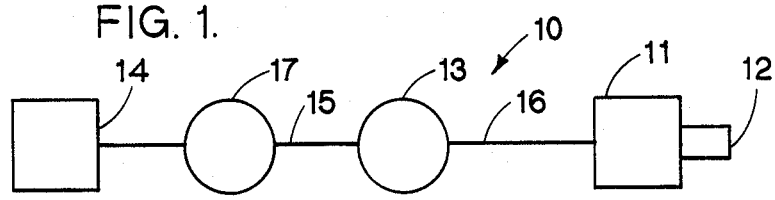
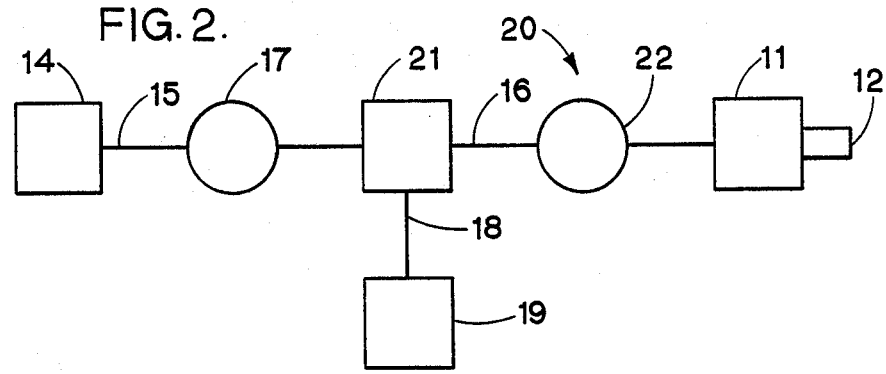
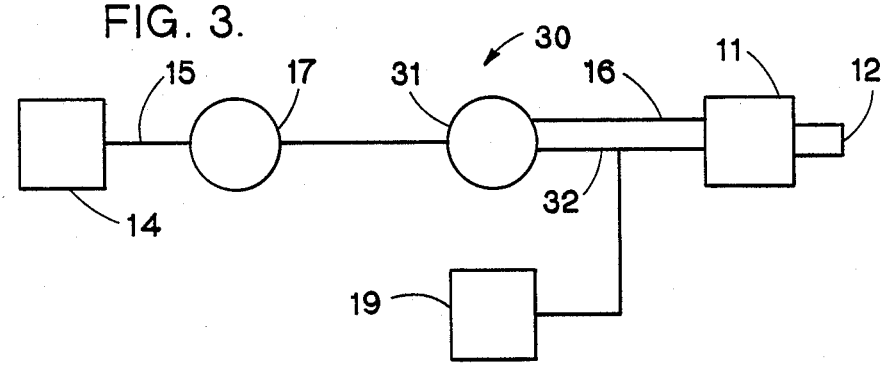
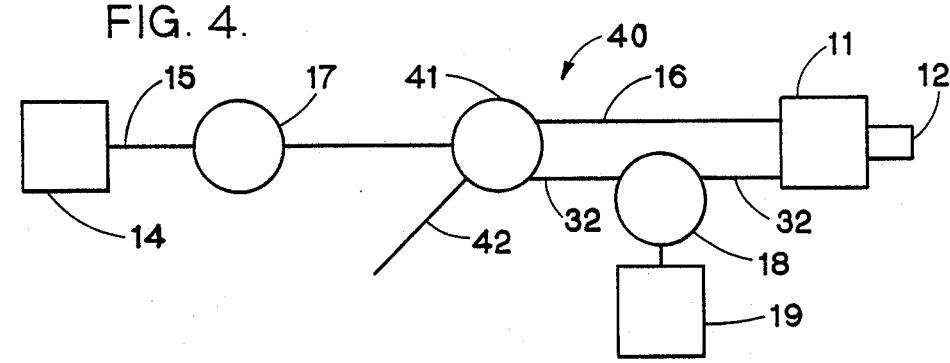

SOUND PRODUCING INDICATORS USED IN COMBINATION WITH PNEUMATICALLY OPERATED MACHINES

BACKGROUND OF THE INVENTION

The invention set forth in this specification pertains to a new and improved combination of an indicator and a pneumatically operated machine. More precisely it pertains to indicators used with such machines to provide a signal or indication (1) only when such a machine is operated in the reverse of the normal manner in which it is operated, (2) is not being operated or (3) when such a machine is either being operated in such a reverse manner or is not being operated at all.

Virtually everyone is familiar with the fact that indicators capable of producing an audible signal are often used with various items of equipment in order to provide a warning when such items of equipment are operated in the reverse of the manner in which they are normally operated. Thus, various types of trucks and other vehicles are frequently provided with a bell type mechanism which is actuated when such a vehicle is operated in reverse. The use of such an indicator is often quite desirable in order to minimize the possibility of an accident occurring.

Normally such indicators or indicator mechanisms as noted are comparatively complex and/or complicated type devices involving more than a very few comparitively simple parts. Since the cost of a comparatively complex indicator is usually quite minor as compared to the cost of a large item of equipment such as, for example, a truck, a bus or a vehicle especially constructed to serve a specialized construction purpose the cost of an indicator normally is not a significant deterrent to the use of an indicator with such vehicles and various other related machines.

However, this is not the case when it is desired to use an indicator to provide an audible signal to indicate that a comparatively small or simple, relatively inexpensive machine is being operated in other than a normal manner, has been stopped or is either not being operated at all or is not being operated in such a manner. Such a simple machine can be defined as a mechanical system of mechanical parts which are connected together so as alter, transmit and direct an applied force in a predetermined manner in order to accomplish a specific objective. Normally the objective is useful work. Frequently conventional indicators for providing an audible signal as discussed in the preceding are or can be nearly or more expensive than a comparatively simple machine.

In cases such as this there is a tendency not to use an audible indicator because of the cost of the indicator as compared to the cost of the machine. While often times there is no significant need to use an audible indicator with a machine on other occasions there is often a real need to use such an indicator with a simple or comparatively simple machine. Usually this need is particularly pronounced in a case where there there is a distinct possibility of damage or harm resulting from a machine being operated in the reverse of the normal manner in which it is operated.

These factors can be illustrated in connection with a presently preferred application of the invention in the field of dental drills or drilling machines. Frequently these are comparatively simple pneumatic devices which use compressed air from a source of the latter to drive a simple air motor which is coupled to or holds a drill bit. As a result of factors which are unimportant to the present invention if bits such as are used in the placement of artificial tooth roots or bodies are rotated in reverse there can be a significant danger of damage to the mouth of a dental patient.

If an indicator was used with such a drilling machine a dentist in using the drill would be immediately aware of the fact that the drilling machine was being operated in reverse if for any reason the machine should be operated in such a reverse manner. As a result of this a dentist would be able to take remedial action so as to avoid damage or any further damage before any significant harm was done if a drill should be operated in other than an intended or normal manner.

Unfortunately it is considered that audible indicators indicating a reverse or other than intended manner of operation of dental drilling machines have not normally been used or have not been used at all in the past. Although the precise reason or reasons for this are not known it considered that cost has been a material factor in preventing the use of audible indicators to provide an indication when a drill or drilling machine is not being operated in a normal or "forward" manner.

BRIEF SUMMARY OF THE INVENTION

As a result of factors as discussed in the preceding it is considered that there is a need for new and improved indicators for use in connection with comparatively simple machines. More specifically it is considered that there is a need for indicators which are comparatively inexpensive and which when used in combination with a machine will reliably provide an audible signal or indication that the machine is being operated in a reverse of its normal manner of operation, is not being operated or is either not being operated or is being operated in such a reverse manner.

Broadly the present invention is intended to provide indicators in combination with machines in order to fulfill this need. The invention is not as broad as this would indicate. It is only applicable to the combination of an audible indicator with a pneumatically operated machine since it pertains to the use of the pneumatic fluid to both operate the machine and to operate the indicator as subsquently described. The invention is intended to provide combinations of such indicators and machines which can be constructed without difficulty at a comparatively nominal cost and which can be operated without significant danger of breakdown for prolonged periods with little or no maintenance.

To avoid any possible misunderstanding it is considered that it is necessary to indicate what is meant in this specification by the word "pneumatic" as used in the preceding paragraph. This is because this term is often used in either or two different manners. It is most commonly used to designate a machine which is operated using a stream or flow of a fluid such as compressed gas. Usually the gas is air. It is used in this specification in a somewhat broader manner to also designate the use of a vacuum to operate a machine. This is because in a sense a vacuum motor is operated by a stream or flow of gas at less than atmospheric pressure resulting from an item such as a vacuum pump removing a fluid, normally a gas, from a chamber or line or the like.

In accordance with this invention the objectives of the invention indicated or suggested in the preceding discussion are achieved by providing in the combination of a machine which is capable of being operated in a first manner by a fluid at other than ambient pressure, conduit means connected to said machine for conveying a fluid relative to said machine so as to operate said machine in said first manner and indicator means for providing an audible signal when said machine is employed in another manner than said first manner the improvement which comprises:

said indicator including a sound producing means capable of being operated by said fluid to produce a sound, said indicator means also including diverting means for diverting at least some of said fluid to said sound producing means so as to operate said sound producing means when said machine is being employed in said other manner in order to indicate that said machine is being employed in said other manner.

BRIEF DESCRIPTION OF THE DRAWING

Because of the nature of this invention it is best more fully described with reference to the accompanying drawing in which:

FIG. 1 is a diagrammatic view of a first embodiment of or of mode or practicing the present invention;

FIG. 2 is a diagrammatic view of a seocnd embodiment of or mode of practicing the invention;

FIG. 3 is a diagrammatic view of a third, presently preferred embodiment of or mode of practicing the invention; and FIG. 4 is a diagrammatic view of a fourth embodiment of or mode of practicing the invention.

The designation of FIG. 3 of the drawing as illustrating a presently preferred embodiment of the invention is not to be considered that the specific embodiment shown in this FIGURE is or will be considered as preferred at all times. It is currently believed that which of the various embodiments illustrated will be preferred for a given application or will be a matter of design choice. Because of this in a sense all of the embodiments of the invention illustrated can be considered as "preferred".

The present invention is not to be considered as being limited by the drawing and is to be considered to be limited solely by the appended claims. The latter are intended to define the scope of protection of the invention whereas the former is merely intended as an aid to the explanation of the invention. Those skilled in the design and use of various pneumatic machines such as pneumatic drills will realize the the principles or concepts of the invention as defined in the claims can be easily applied in many different pneumatic machines through the use or exercise or routine skill in the noted field on the basis of the teachings of this specification.

In the subsequent description of the various embodiments of the invention illustrated in the drawing the same numerals have been used to designate like parts in the various embodiments illustrated in the interest of brevity. Such parts are not separately described in the subsequent description and are mentioned only when this is considered necessary to an understanding of the invention.

DETAILED DESCRIPTION OF THE PREFERRED EMBODIMENTS

In the FIG. 1 of the drawing there is shown a combined structure 10 which includes a pneumatically operated machine 11 such as a common dental drill motor having an extended shaft 12 such as is used to hold a dental drill (not shown) which is adapted to be turned in a specific or first direction when the machine 11 is operated. This machine 11 is used in combination with a conventional control valve 13 capable of being operated in a known manner in order to allow a pneumatic fluid (not shown) to flow from a conventional pneumatic or vacuum source 14 of such a fluid through a line 15 and the valve 13 to another line 16 connecting the machine 11 with the valve 13. A conventional on-off valve 17 can be located in the line 15 if desired. Similarly conventional auiliary items such as a pressure regulator (not shown) and a filter (not shown) can be located in this line 15.

The valve 13 is of such a character that when it is adjusted so that a pneumatic fluid is not being provided to the machine 11 the fluid will be provided through another line 18 to an indicator or device 19 capable providing an audible signal in response to the presence of the fluid. Normally such a fluid will be compressed air. When this is the case preferably the device 18 is a common whistle or whistle-like horn. Such a whistle or whistle-like structure is preferred since such a structure is simple, inexpensive and capable of satisfactorily operating satisfactorily for a prolonged period without maintenance even when various particles or liquids may have accumulated on it to a moderate degree.

It is believed that the operation of the structure 10 will be obvious from the preceding discussion and from a consideration of the various parts indicated. During the normal operation of machine 11 so as to turn the shaft 12 in a first first or normal direction the valve 17 will be open and the valve 13 will be adjusted so that the pneumatic fluid employed will flow through the valve 13 so as to operate the machine 11. When the valve 13 is operated or adjusted as to cut off the flow of fluid to the machine 11 it will automatically divert the fluid flow to the indicator 18. This will cause the indicator to produce an audible signal indicating that the machine 11 has been stopped.

Substantially the same result can be achieved with a modified structure 20 as shown in FIG. 2. In this modified structure the valve 13 is replaced by a conventional pressure responsive valve 21 which will allow the pneumatic fluid used to flow to the line 18 only when there is a pressure rise in the valve 21 and the line 15 to above the pressure present when the machine 11 is being operated. When there is a flow to the line 18 the indicator 19 will be operated by the fluid flowing to it. Such a pressure rise will normally be caused by a conventional on-off valve 22 corresponding to the valve 14 being closed. When this valve 14 is closed pneumatic fluid will, of course, no longer be supplied to the machine 14 and, of course, the shaft 12 will no longer be rotated.

In FIG. 3 there is a shown a structure 30 which is considered to be particularly adapted for use with dental drills and the like. It is substantially the same as the structure 10 previously described except for the replacement of the valve 13 with another valve 31 and the addition of a line 32 in parallel with the line 16 between the valve 31 and the machine 11. In the structure 30 the machine 11 is capable of being operated in reverse when fluid is supplied to it through the line 32. The line 18 is connected to this line 32.

In the structure 30 the machine 11 is constructed in a conventional manner so that "spent" fluid used to operate it supplied by through either the line 16 or 32 is vented to the ambient at and by the machine 11. This valve 31 is a conventional valve which can be used in order to direct pneumatic fluid from the source 14 to either the line 16 or the line 32. When fluid is supplied to the line 32 such fluid will flow to the indicator 19 through the line 18 so as to operate the indicator 19. Preferably the valve 31 is also constructed in a conventional manner to serve as a shut off valve so that there is no flow through it from the lines 16 and 32.

The operation of the structure 30 is similar to the operation of the various structures 10 and 20 described in the preceding. When the machine 11 is operated in a normal manner by passing a pneumatic fluid to it through the line 16 the indicator 19 will not be used. When the flow is changed so that the machine 11 is operated in reverse by fluid passing through the line 32 the alarm indicator 19 will automatically be operated so as to produce an audible warning sound.

The structure 40 shown in FIG. 4 of the drawing is almost identical to the structure 30 described in the preceding. It differs from the structure 30 in that the machine 11 is not intended to vent spent pneumatic fluid to the ambient but is intended to return such fluid to a valve 41 corresponding to the valve 31 through the line 16 or 32 which is not used to supply the motor 11 with pressurized fluid. The valve 41 is a conventional valve which includes a vent or return line 42 which is normally used to vent fluid which has been used to operate the motor 11 to the ambient. The valve 41 is also constructed so that when fluid is supplied to the motor 11 through the line 32 so as to operate it in reverse some of the pressured pneumatic fluid from the source 14 will be directly supplied to the indicator 19 through the line 18. This mode of operation of course requires that the line 18 be connected directly to the valve 18.

I claim:

1. In the combination of a machine which is capable of being operated in a first manner by a fluid at other than ambient pressure, conduit means connected to said machine for conveying a fluid relative to said machine so as to operate said machine in said first manner and indicator means for providing an audible signal when said machine is employed in another manner than said first manner the improvement which comprises:

said indicator including a sound producing means capable of being operated by said fluid to produce a sound, said indicator means also including diverting means for diverting at least some of said fluid to said sound producing means so as to operate said sound producing means when said machine is being employed in said other manner in order to indicate that said machine is being employed in said other manner.

2. The combination claimed in claim 1 where:
said machine has a movable member which moves in said first direction when said machine is being operated and which moves moves in the opposite direction when said machine is employed in said other manner,
whereby said sound producing means is operated only when said movable member is being operated in said other direction.

3. The combination claimed in claim 3 wherein:
said machine is a rotary drill and said member is a drilling bit, and
said fluid is a pressurized pneumatic fluid.

4. The combination claimed in claim 4 wherein:
said machine is a rotary drill and said member is a drilling bit, and
said fluid is a gas at less than normal ambient pressure.

5. The combination claimed in claim 1 wherein:
said machine has a movable member which moves in said first direction when said machine is being operated and which does not move when said machine is employed in said other manner,
whereby said sound producing means is operated only when said movable member is operated in said other direction.

6. The combination claimed in claim 5 wherein:
said machine is a rotary drill and said member is a drilling bit, and
said fluid is a pressurized pneumatic fluid.

7. The combination claimed in claim 5 wherein:
said machine is a rotary drill and said member is a drilling bit, and
said fluid is a gas at less than normal ambient pressure.

8. The combination claimed in claim 1 wherein:
said machine has a movable member which moves in said first direction when said machine is being operated and which does not move when said said machine is employed in said other manner, or which either does not move or moves in another direction when said machine is operated in said other manner.
whereby said sound producing means is operated only when said movable member is operated in said other direction.

9. The combination claimed in claim 8 wherein:
said machine is a rotary drill and said member is a drilling bit, and
said fluid is a pressurized pneumatic fluid.

10. The combination claimed in claim 8 wherein:
said machine is a rotary drill and said member is a drilling bit, and
said fluid is a gas at less than normal ambient pressure.

* * * * *